United States Patent [19]  [11] 4,219,440
Runck et al.  [45] Aug. 26, 1980

[54] MULTIPLE ANALYSIS HEMATOLOGY REFERENCE CONTROL REAGENT AND METHOD OF MAKING THE SAME

[75] Inventors: Alan H. Runck, Hollywood; Douglas Armstrong, Coral Springs; James T. Hutchisson, Miami Springs, all of Fla.

[73] Assignee: Coulter Electronics, Inc., Hialeah, Fla.

[21] Appl. No.: 44,841

[22] Filed: Jun. 6, 1979

Related U.S. Application Data

[63] Continuation-in-part of Ser. No. 915,761, Jun. 15, 1978, abandoned.

[51] Int. Cl.$^2$ .................. G01N 33/16; C09K 3/00
[52] U.S. Cl. .................. 252/408; 23/230 B; 356/39; 356/42; 424/3; 424/101; 424/322
[58] Field of Search .................. 23/230 B; 252/408; 424/3, 101, 322; 356/39, 42

[56] References Cited

U.S. PATENT DOCUMENTS

| | | | |
|---|---|---|---|
| 3,406,121 | 10/1968 | Jones | 252/408 |
| 3,466,249 | 9/1969 | Anderson | 252/408 |
| 3,634,581 | 1/1972 | Thomas | 252/408 |
| 3,640,896 | 2/1972 | De Casperis | 252/408 |
| 3,682,835 | 8/1972 | Louderback | 252/408 |
| 3,714,345 | 1/1973 | Hirata | 252/408 |
| 3,873,269 | 3/1975 | Kraffczyk et al. | 252/408 |
| 3,873,467 | 3/1975 | Hunt | 252/408 |
| 3,874,852 | 4/1975 | Hamill | 252/408 |
| 3,962,125 | 6/1976 | Armstrong | 252/408 |
| 3,977,995 | 8/1976 | Louderback et al. | 252/408 |
| 4,145,185 | 3/1979 | Brinkhous et al. | 252/408 |
| 4,157,383 | 6/1979 | Sedlacek et al. | 252/408 |
| 4,160,644 | 7/1979 | Ryan | 252/408 |

OTHER PUBLICATIONS

Davis, J. W., et al., Blood, vol. 39, No. 3, pp. 388–397, (1972).
Owen, J. D., Biochim. Biophys. Acta., vol. 443, pp. 306–309, (1976).
Wertz, R. K., et al., Am. J. Clin. Path., vol. 68, pp. 195–201, (1977).
C. A., vol. 71, p. 109, 28490z, (1969).
C. A., vol. 69, p. 869, 9269b, (1968).
Saunders, A. M., et al., J. Histochem. Cytochem., vol. 22, pp. 707–710, (1974).

*Primary Examiner*—Teddy S. Gron
*Attorney, Agent, or Firm*—Silverman, Cass & Singer, Ltd.

[57] ABSTRACT

A single diagnostic test reagent for use as a multiple-analysis hematology reference control for monitoring the precision and accuracy of measurements or determinations of red blood cell, white blood cell and platelet blood cell counting, hemoglobin content, hematocrit, mean cell volume and mean platelet volume determination, red cell distribution width and platelet distribution width determination, and determination of mean corpuscular hemoglobin, mean corpuscular hemoglobin concentration, and thrombocytocrit. The control reagent includes ingredients for monitoring platelet parameters also notwithstanding that potential interfering effects of red blood cells normally observed in blood specimens also are present in the control reagent. The control reagent is suitable for use in automated or semi-automated hematology instruments and by users of manual methodologies.

The invention includes a method of making said control reagent.

21 Claims, No Drawings

MULTIPLE ANALYSIS HEMATOLOGY REFERENCE CONTROL REAGENT AND METHOD OF MAKING THE SAME

CROSS-REFERENCE TO RELATED APPLICATIONS

This application is a continuation-in-part of our application Ser. No. 915,761 filed June 15, 1978, now abandoned, entitled MULTIPLE ANALYSIS HEMATOLOGY REFERENCE CONTROL REAGENT AND METHOD OF MAKING THE SAME, this application being owned by the assignee hereof.

BACKGROUND OF THE INVENTION

This invention concerns a stable hematology reference control reagent suitable for use in common medical diagnostic procedures to analyze and test a patient's blood sample for making classic determinations with respect to the blood sample and more particularly, provides a novel diagnostic test control reagent which includes ingredients providing the control reagent with the capability of monitoring the desired platelet parameters of the patient's blood sample as well as the seven classic determinations or parameters with respect to the blood sample. In other words, the invention provides a single hematology reference control reagent which can be used for monitoring the precision and accuracy of the classic hematology measurements or determinations, i.e., red blood cell count (RBC), white blood cell count (WBC), hematocrit (HCT), the hemoglobin (HGB), the mean corpuscular hemoglobin (MCH), the mean corpuscular volume (MCV) and the mean corpuscular hemoglobin concentration (MHC) and as a control also for monitoring the accuracy and precision of the measurement and determination of platelet parameters such as platelet count, mean platelet volume, platelet volume fraction (thrombocytocrit) and platelet distribution width using the same whole blood product that is conventionally used for the control for the previously mentioned classical hematology parameters.

It is a common medical diagnostic procedure to analyze and test a blood sample of a patient in order to make certain classic determinations with respect to the blood sample. This procedure is an important diagnostic tool for the physician. As a result of modern technological advances, there have been automated instruments developed which will accept a patient's blood sample and process the sample automatically and continuously to provide the parameters or determinations described above as the seven classic parameters of a blood sample. An instrument which will accept a patient's blood sample and process same automaticlly and continuously to provide these seven classic parameters or determinations enumerated is described and claimed in U.S. Pat. No. 3,549,994. Said U.S. Pat. No. 3,549,994 provides acceptable definitions of such parameters and illuminates the problems to be solved in handling of the blood sample as it is drawn through the fluid system of said patented apparatus.

Coulter Electronics, Inc. of Hialeah, Fla., the assignee of this patent application, also manufactures and sells other blood cell counting and analyzing instruments which are less sophisticated than the apparatus of said U.S. Pat. No. 3,549,994 but which are operated to determine red blood cell and white blood cell counts, hemoglobin concentration and their collected indices such as HCT, MCV, MCH and MCHC.

In the use of such an instrument which may be referred to herein, at times, by the registered trademark "COULTER COUNTER" owned by Coulter Electronics, Inc., there is required to be employed a multipurpose diluent comprising an electrolyte which enables electronic measurements to be made by the COULTER COUNTER ® instrument. A suitable multi-purpose diluent for use in blood analysis by an electronic instrument such as the COULTER COUNTER ® is described and claimed in U.S. Pat. No. 3,962,125.

A suitable reagent for determining leukocytes and hemoglobin in the blood sample by means of a high speed automated hematology instrument such as the COULTER COUNTER ®is described in U.S. Pat. No. 3,874,852 issued Apr. 1, 1975. The reagent described and claimed in said patent is a lysing reagent for converting hemoglobin to a chromogen for making the desired determinations.

Coulter Electronics, Inc. has heretofore provided a hematology reference control for accuracy in electronic estimation of blood cell values capable of functioning with the diluent and lysing reagents discussed above. One such reference control has been sold by Coulter Electronics under its registered Trademark 4C which comprises a modified whole blood hematology reference control prepared from fresh human blood. Fixed erythrocytes were added to simulate leukocytes. This reference control had seven known blood values which were stable for a desired period of time. The reference control was prepared for use with the COULTER COUNTER ® and accessory mean corpuscular volume hematacrit computers and hemoglobinominators. When used with the blood diluent identified above, it served as a check on accuracy of dilution, red blood cell counts, and MCV-Hematocrit computer calibration. After addition of a lysing reagent, the reference control served as a check on white blood cell counts. Thus, the so-called 4C ® hematology reference control was utilized in the COULTER COUNTER ® for electronic estimation of red and white blood cells, hematocrit, mean corpuscular volume, hemoglobin, mean corpuscular hemoglobin and mean corpuscular hemoglobin concentration. Other hematology reference controls also were available for use with the COULTER COUNTER ® which comprise stabilized human red blood cell suspensions such as the product known as Baker Haem-C ® of J. P. Baker Chemical Corporation or the product known as CH-60 ® of the Dade Reagent Company of Hialeah, Fla. However, none of these mentioned hematology control reagents were capable of being used for testing accuracy of measurements of platelet parameters. Consequently, for making such determinations, a separate control had to be employed for monitoring the platelet parameters. In other words, a separate control had to be employed for making the platelet determinations and the hematology control reagents for making the seven classical measurements or parameter determinations could not be employed for platelet control functions.

Further, prior art platelet counting has been inadequate because of the lack of stable platelet controls containing other blood components, namely, red blood cells. Thus, the increasing availability of instrumentation for distinguishing platelets from red blood cells and automatically performing platelet counts has created a great need for stable control products which contain both platelets and red blood cells.

The single hematology control of this invention includes the capability of monitoring platelet parameters as well as the seven classic parameters of hematology measurements. This hematology control has the advantage in that it eliminates the need for a separate control material for monitoring platelet parameters and provides a more meaningful determination of platelet parameters in that the potential interfering red blood cells, red blood cell metabolites, etc., normally observed in patient blood specimens are present in the control material of the invention. This is especially important for platelet counts performed with manual methodologies using light microscopy or phase microscopy, where great skills on the part of laboratory technologists is required to adequately differentiate blood platelets from red blood cells and other cellular materials. The subject invention also provides a means for monitoring these measurements using manual methodology or automated or semi-automated hematology instruments for hematology measurements along with a means for testing accuracy of platelet count, mean platelet volume, platelet volume fraction (thrombocytocrit) and platelet distribution based on the use in the reference control of the present invention of the same whole blood product which is conventionally used for control of the classic seven hematology parameters.

SUMMARY OF THE INVENTION

This invention consists of a stable whole blood control containing platelets prepared by adding freshly procured human blood platelets or animal blood platelets either natively drawn or preserved through chemical or physical fixation to a conventional, commercially available whole blood hematology control, such as said 4C ®, Baker Haem-C ® or Dade CH-60 ®. Such heretofore conventional, commercially available whole blood hematology control reagents are conditioned in accordance with the invention by adding sodium chloride and urea. The sodium chloride and urea may be added directly to the whole blood control or may be dissolved first in water and then added to the whole blood control. The components are present and/or are added in proportion such that the values for WBC, RBC, HGB, HCT, MCV, MCH, MCHC, red cell distribution width, platelet count, mean platelet volume, thrombocytocrit and platelet volume width distribution approximate those found in normally occurring human blood specimens and which can be measured by using a variety of known manual or automatic instrumentation methodologies. The suspension medium can comprise an artificial medium, human or animal plasma or animal protein solutions.

The 4C ® product of Coulter Electronics, Inc. is a stable reference control which was especially suitable for use with the COULTER COUNTER ® instrument when establishing standards of quality control for the performance of the instrument. A correctly calibrated and functioning instrument is utilized to provide the seven measured or calculated parameters within a range of expected results when the 4C ® is used.

Also, the invention encompasses the disclosed method of making the stable reference control.

DETAILED DESCRIPTION OF THE INVENTION

This invention utilizes a combination of urea and sodium chloride as (1) a stabilizing agent for use with whole blood controls that include platelets and (2) an inhibitor of the detrimental effects of animal and human red blood cell metabolites, by-products, and chemicals inherent to the red blood cell and white blood cell on animal and human platelets.

Urea alone previously has been employed as a stabilizing agent in pure suspensions of human blood platelets prepared as a control material to be used in connection with performing platelet counts. The human blood platelets prepared in this manner have been essentially in pure suspensions; no residual red blood cells or white blood cells have been allowed to be present in such controls. The function of the added urea in such control suspensions simply has been to prevent the gradual disintegration of the platelets during subsequent storage over a period of time equaling several months. The overall effect has been to provide a suspension of platelets that remains relatively constant ($\pm 20\%$) in the number of blood platelets per unit volume. If the urea were not added, the number of particles per unit volume would gradually increase as the platelets began to disintegrate usually within several days.

Heretofore, red blood cells and white blood cells have not been allowed to be present in platelet controls. The reason is believed to be that these cells almost immediately cause platelets to aggregate and disintegrate, thereby destroying the effectiveness of the mixed control material. In addition, urea in high concentrations was known to be detrimental to the stability and integrity of red blood cells, thereby apparently precluding its use as a preservative in suspensions containing red blood cells. As a result, prior known platelet controls have consisted simply of pure suspensions of human platelets in the presence of urea as a preservative, no red blood cells or other formed elements of the blood having been allowed to be present, thereby diminishing their effectiveness as control materials.

Until the present invention, there have been no known successful combinations of whole blood reference controls that contain preserved human platelets stabilized with two molar urea. In fact, present art teaches that when two molar urea employed in this invention is added to human blood cells, the red blood cells are destroyed (Owen, J. D., "Computer Simulated Urea Reflection Coefficients In Human Red Blood Cells," Biochem. et Biophys. Acta 443, 306–310, 1976; Saunders, A. M., Scott, F., "Hematologic Automation By Use Of Continuous Flow Systems," J. Histochem. Cytochem. 22, 707–710, 1974).

We have discovered that urea in the presence of sodium chloride serves to prevent the deleterious effect of autologous red blood cells and white blood cells on blood platelets in the suspension. Consequently, we provide a stable blood platelet suspension that contains red blood cells and approximates the composition of human blood. There is provided a single stable suspension which contains both blood platelets and red blood cells, made possible through the use of a combination of urea and sodium chloride which is added to previously stabilized human red blood cell suspensions, such as Coulter 4C ®, Baker Haem-C ®, or Dade CH-60 ®, which can easily tolerate the otherwise detrimental effects of urea. The combination of urea, saline and the previously preserved red blood cell suspension is itself uniquely stable and provides a compatible medium in which either native blood platelets or blood platelets that have been fixed using formaldehyde, glutaraldehyde, osmic acid or other chemical fixative agents can coexist in stable form.

Another derived benefit of this invention is that the combination of urea, saline and previously fixed red blood cell suspensions provides an environment in which the cell volume of individual blood platelets remain unchanged. By use of a combination blood platelet and red blood cell control suspension, it is now possible for laboratories to monitor the accuracy of platelet count, mean platelet volume (MPV) and platelet volume distribution (PDW) measurements, so that effective patient measurements may be performed on a routine basis.

A whole blood control containing platelets according to the invention was prepared by mixing conventional, commercially available whole blood control products such as Coulter 4C ®, Baker Haem-C ® or Dade CH-60 ® with freshly collected or chemically preserved human blood platelets or animal blood platelets and a mixture of urea and sodium chloride. After stabilizing for several days, the suspension was found to have stable values for the hematology parameters WBC, RBC, HGB, MCV, HCT, MCH, MCHC, red cell distribution width, platelet count, mean platelet volume, thrombocytocrit and platelet volume distribution width. The detrimental effects of the red blood cells and white cell analogs present in the whole blood controls used as substrate was prevented by the addition of sodium chloride and urea and the material could be used as a stable control for several months.

METHOD OF PREPARING CONTROL REAGENT

The first step, in one mode of preparing a whole blood platelet control of this invention was to procure a volume of conventionally manufactured whole blood hematology reference control material such as Coulter 4C ®, Baker Haem-C ® or Dade CH-60 ®, or any other commercially manufactured or other suitable whole blood hematology control material comprising treated erythrocytes in an artificial medium. Then human or animal blood platelets were procured through venipuncture or other bleeding procedure of the donor human or animal subject. The human or animal blood platelets can then be used in any manner whatsoever either as freshly obtained or after any of the chemical or physical fixative procedures have been applied to the platelets.

The next step was to prepare a solution or urea and sodium chloride in water or other vehicle for subsequent mixing with the whole blood control and the platelets. In the solution, the urea and sodium chloride are added in the following relationship, generally, to 1000 ml of medium, e.g., water, Urea—120 gms
Sodium Chloride—9 gms Variations in urea used in one liter of medium range between 100 and 140 gms and sodium chloride between 8 and 10 gms. The urea and sodium chloride were either mixed with each other and subsequently added to the control suspension or were dissolved in approximately one liter of medium, e.g., water, (for example,) and the resulting solution added at that time to the control material in amounts to be discussed hereinafter. A salt equivalent to sodium chloride may be utilized.

The final step was to simply mix the commercially or individually prepared whole blood hematology reference control, the untreated, unstabilized or previously stabilized platelet suspension and the solution of urea and sodium chloride together. After mixing for approximately 30 minutes, and allowing the cell suspension to stabilize for approximately 48 hours, the control material was stable for complete hematoloty parameters, as stated. A selective suspension of red blood cells and platelets is realized. The suspension medium can be artificial, or a human or animal plasma or human or animal protein solutions.

The following examples show how suspensions of treated red blood cells, platelets and solutions of sodium chloride and urea can be mixed together to provide the whole blood control of the present invention, as described:

(1) A solution containing 24 grams of urea and 1.8 grams of sodium chloride in 200 ml of distilled water is added to 1000 ml of a treated whole blood suspension such as Coulter 4C ®.

A solution containing 2.4 grams of urea and 0.18 grams of sodium chloride in 20 ml of distilled water is added to 100 ml of a human platelet suspension.

Each resulting suspension is mixed for several minutes and then treated red blood cell suspension and platelet suspension, both containing urea, are mixed with each other thoroughly for approximately thirty minutes and allowed to subsequently stabilize for approximately 48 hours to provide the reference control of this invention.

(2) 20.0 grams of urea and 1.5 grams of sodium chloride are directly added to 1000 ml of a treated whole blood suspension such as Coulter 4C ®. 100 ml of a human platelet suspension is then directly added to the treated whole blood control suspension containing urea and sodium chloride. The suspension is mixed for approximately 30 minutes and allowed to stabilize for 48 hours to provide the reference control of this invention. It will be noted from this embodiment that it is not required to solublize the urea and sodium chloride prior to admixture with the treated whole blood suspension.

(3) A solution containing 26.6 grams of urea and 1.98 grams of sodium chloride in 220 ml of distilled water is directly added to 1000 ml of a treated whole blood control suspension such as Coulter 4C ®. 100 ml of a human platelet suspension is then added. The resulting suspension is mixed for approximately 30 minutes and allowed to stabilize for 48 hours to provide the reference control of this invention.

In the reference control of the present invention, urea is present in the relationship of between about 16.7 to about 23.3 grams in approximately one liter of the reference control of the invention.

Also, in the reference control of the invention, sodium chloride is added, in relation to the urea concentration, i.e., 1.33 to 1.67 grams sodium chloride to each liter of reference control containing the aforementioned 16.7 to 23.3 grams of urea.

It is to be understood that this added amount of sodium chloride is additional to the residual salinity of the treated whole blood suspension or platelet suspension to which same is added. It will further be understood that the significant factor in accordance with the invention, is the relationship between the urea and the added sodium chloride, not the total salinity of the reference control.

It is this relationship between the urea and the added sodium chloride that enables the preparation of a stable reference control containing at least both red blood cells and platelets.

The following will be noted with respect to the effect and importance of added sodium chloride. Most starting materials used in the present suspension, stabilized blood controls and platelet suspensions contain previously added sodium chloride. The invention describes adding a mixture of urea and sodium chloride to these materials so that they may co-exist. The purpose of the added sodium chloride is to maintain the osmotic and ionic balance when urea is added.

One should consider that there exists an independence of cell count (platelets, red blood cells and white blood cells) and cell characteristics (mean cell volume, and cell morphology) from chemical composition of the reference control of the invention. The chemical composition of the reference control of the invention consisting of previously stabilized red blood cells and fixed red blood cells, platelets, and added urea and added sodium chloride, is independent of the desired cell count and cell characteristics. For example, the invention allows approximately 100 ml of a suspension containing either very many platelets or very few platelets to be added to approximately 1000 ml of an existing whole blood control such as Coulter 4C ® having a high or low red blood count in white blood count value, in the high or low mean cell line value so that the resulting approximate volume of 1100 ml of cell suspension has relatively few or many platelets, red blood cells and white blood cells, depending upon the levels desired.

As used in the art and in this specification, the terms "stabilized" and "treated" as applied to blood cells, are synonymous and are contrasted with the term "fixed cells." Both the initial starting materials described in this invention (the previously stabilized cell control and the platelets) can consist of either stabilized or treated cells, chemically fixed cells or native untreated cells.

For example, Coulter 4C ® consists of stabilized (treated) red blood cells and chemically fixed red blood cells.

Stabilized (treated) cells consist of human or non-human cells to which various preservatives have been added to prolong their life.

Chemically fixed cells consist of human or non-human cells which have been chemically hardened, i.e., tanned, usually by chemicals such as glutaraldehyde, formaldehyde, osmic acid or uranyl acetate.

Stabilized cells are generally susceptible to hemolysis or disruption in the presence of surfactants or low osmolality, while chemically fixed cells retain their morphology under such environments.

As explained, the hematology reference control embodying the invention was suitable for use in making manual determinations as well. Persons skilled in the art know the methodologies used for manual determinations of RBC, WBC, HGB and HCT using such control reagents. It is believed unnecessary to explain in detail these manual methodologies, it being sufficient to appreciate that the reference control of the invention can be used both for instrumentation and manual methodologies, as described herein.

We claim:

1. A multiple analysis hematology reference control comprising a suspension of red blood cells and platelets in a saline medium which includes urea, said urea being present in at least a concentration normally detrimental to stability and integrity of red blood cells, said urea concentration not causing deleterious effects such that red blood cell and platelet parameters are generally stable and approximate those occurring in mammalian blood specimens, wherein said control is capable of being used for testing the accuracy and precision of classical red blood cell and platelet parameters.

2. A reference control as described in claim 1 in which said medium is an artificial one.

3. A reference control as described in claim 1 in which said medium is a human or animal blood plasma.

4. A reference control as described in claim 1 in which said medium is a human or animal protein solution.

5. A reference control as described in claim 1 in which said platelets are of human or animal origin.

6. A reference control as described in claim 1 in which the urea is present in the ratio of between about 16.7 to 23.3 grams in approximately 1 liter of the reference control.

7. A reference control as described in claim 6 in which sodium chloride is added in the ratio of between 1.33 and 1.67 grams to approximately one liter of the reference control.

8. A multiple analysis hematology reference control comprising a single suspension of red blood cells and platelets, said suspension including urea and sodium chloride in a selected suspension medium which enables use of the control for monitoring the accuracy and precision of measurements or determinations of classical hematology parameters and platelet parameters of blood sample, said urea being present in at least a concentration normally detrimental to stability and integrity of red blood cells, said urea concentration not causing deleterious effects such that red blood cell and platelet parameters are generally stable and approximate those occurring in mammalian blood specimens, wherein said reference control is capable of being used for testing the accuracy and precision of classical red blood cell and platelet parameters.

9. A reference control as described in claim 8 in which said medium is an artificial one.

10. A reference control as described in claim 8 in which said medium is a human or animal blood plasma.

11. A reference control as described in claim 8 in which said medium is a human or animal protein solution.

12. A reference control as described in claim 8 in which said platelets are of human or animal origin.

13. A reference control as described in claim 8 in which the urea is present in the ratio of between 16.7 and 23.3 grams in approximately one liter of the reference control.

14. A reference control as described in claim 13 in which sodium chloride is added in the relationship of between 1.33 and 1.67 grams in approximately one liter of said reference control.

15. A method of making a single hematological reference control for monitoring the accuracy of measurements of both conventional hematology parameters and platelet parameters comprising;

(A) preparing a stabilized suspension of human or animal blood platelets;

(B) procuring a conventional whole blood hematology reference control comprising erythrocytes in a suspension medium;

(C) mixing the stabilized platelet suspension and the reference control with a mixture of urea and sodium chloride or the like salt selected to be compatible with the hematology components of the mixture for a preselected period of time; and (D) allowing the resultant suspension to stabilize for approximately 48 hours, said urea being present in at least a concentration normally detrimental to stability and integrity of erythrocytes, said urea concentration not causing deleterious effects such that erythrocyte and platelet parameters are generally stable and approximate those occurring in mammalian blood specimens.

16. The method as described in claim 15 in which the urea and chloride salt are mixed together and added to the control of paragraph (B) initially.

17. The method as described in claim 15 in which the urea and chloride salt are dissolved in a reasonable volume of water and then added to the control of paragraph (B).

18. The method as described in claim 15 in which a suspension medium is employed which is artificial or of a natural biological character.

19. The method as described in claim 15 in which the urea and chloride salt are dissolved in a reasonable volume of water and then added to the control of paragraph (B) and then the platelet suspension of paragraph (A) added thereto.

20. The method as described in claim 15 in which the urea and chloride salt are added respectively to the control of paragraph (B) and to the platelet suspension of paragraph (A) and the resulting suspensions admixed.

21. The method as described in claim 20 in which the urea and chloride salt are solublized before addition to said control of paragraph (B) and platelet suspension of paragraph (A).

* * * * *